United States Patent [19]
Orchard et al.

[11] Patent Number: 5,169,217
[45] Date of Patent: Dec. 8, 1992

[54] CONTROLLED ENVIRONMENT CHAMBER APPARATUS

[75] Inventors: Kenneth L. Orchard, Beaverton; Frank W. Enderlin, Tigard, both of Oreg.

[73] Assignee: International Portland Corporation, Hillsboro, Oreg.

[21] Appl. No.: 683,331

[22] Filed: Apr. 10, 1991

[51] Int. Cl.⁵ .............................................. A61G 11/00
[52] U.S. Cl. ................................ 312/223.1; 312/223.1
[58] Field of Search ...................... 312/1, 223; 600/21, 600/22; 128/200.27, 200.25, 202.12, 202.16, 205.26

[56] References Cited
U.S. PATENT DOCUMENTS

| | | | |
|---|---|---|---|
| 4,361,137 | 11/1982 | Grosholz | 600/22 |
| 4,846,783 | 7/1989 | Koch et al. | 600/22 |
| 4,936,824 | 6/1990 | Koch et al. | 600/22 |

Primary Examiner—Joseph Falk
Attorney, Agent, or Firm—Dellett, Smith-Hill and Bedell

[57] ABSTRACT

Controlled environment chamber apparatus for maintaining biological material under controlled conditions of temperature and/or humidity comprises a cabinet defining a chamber, a door for controlling access to the chamber, and a clean air source for providing a flow of clean air past the chamber opening.

17 Claims, 2 Drawing Sheets

CONTROLLED ENVIRONMENT CHAMBER APPARATUS

BACKGROUND OF THE INVENTION

This invention relates to controlled environment chamber apparatus.

A controlled environment chamber apparatus, such as a laboratory incubator, typically comprises a cabinet that defines a chamber for receiving biological material. The apparatus is used to provide an environment of controlled temperature and/or humidity for study of the material.

The success of an investigation carried out using a laboratory incubator can be impaired if foreign particles, such as bacteria, enter the incubator chamber, and it is therefore desirable to take steps to prevent entry of airborne particles into the incubator chamber. For example, an incubator may be provided with a door mounted to the cabinet for pivotal movement between an open condition, in which a specimen can be placed in the chamber or removed from the chamber through the chamber opening, and a closed position in which the chamber opening is blocked by the door.

A disadvantage of this type of door is that when it is opened, a region of low pressure is established along the edges of the door and ambient air is drawn toward the chamber opening. If the door stands open for any significant period of time, airborne particles in the ambient air will diffuse into the chamber. There is also a possibility of particles being forced into the chamber when the door is subsequently closed.

SUMMARY OF THE INVENTION

In accordance with the present invention, controlled environment chamber apparatus for maintaining biological material under controlled conditions of temperature and/or humidity comprises a cabinet defining a chamber, at least one door for controlling access to the chamber, the door being mounted to the cabinet for pivotal movement between an open position in which access can be had to the interior of the chamber and a closed position in which the chamber opening is blocked, and a clean air source for providing a flow of clean air past the chamber opening.

BRIEF DESCRIPTION OF THE DRAWINGS

For a better understanding of the invention, and to show how the same may be carried into effect, reference will now be made, by way of example, to the drawings in which.

DETAILED DESCRIPTION

Figure 1:
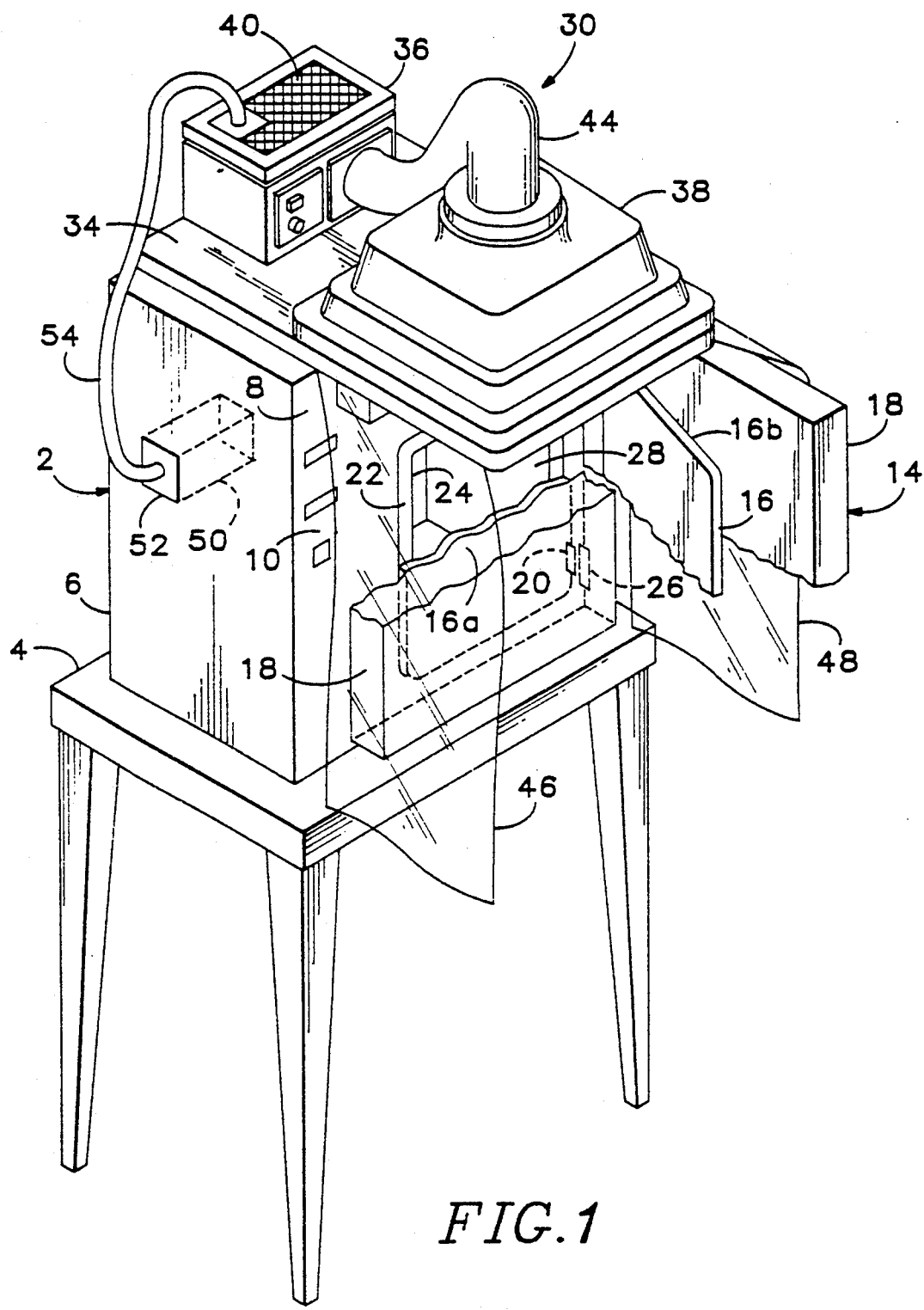
FIG. 1 is a perspective view of a first form of laboratory incubator apparatus embodying the present invention.

FIG. 1 illustrates a laboratory incubator 2 resting on a bench 4. The incubator comprises a cabinet 6, which has a front wall 8 that includes a control panel 10, and a door 14. The door comprises an inner leaf 16 of glass or other transparent material and an outer leaf 18 that has good thermal insulating properties. The inner leaf 16 is attached to the incubator cabinet by a vertical hinge 20, which is shown only schematically in FIG. 1, so that it can be swung between a closed position illustrated by the reference 16a and an open position illustrated by the reference 16a. In the closed position, the leaf 16 engages a sealing gasket 22 that surrounds a chamber opening 24 defined in the front wall 8. The outer leaf is attached to the incubator cabinet by a vertical hinge 26 so that it can be swung between a closed position, in which it closely overlies the inner leaf, and an open position. When both door leaves are in the open position, access can be had to the incubator chamber 28 through the chamber opening 24.

A clean air source 30 is mounted on top of the incubator 2. The clean air source comprises a support frame 34 that is attached to the incubator cabinet 6 by bolts or other suitable fastening elements and extends in cantilever fashion forward of front wall 8 of the incubator cabinet. A fan unit 36 and a filter head 38 are mounted on the support frame using suitable fastening elements. The fan unit and filter head may be of the kind manufactured by International Portland Corporation of Hillsboro, Ore. and sold under the designation CLAS 10 Model 350. The fan unit contains an electrically driven blower which inducts air through a prefilter 40 at the suction side of the blower and delivers it to the filter head 36 by way of a tube 44 connected to the pressure side of the blower. The filter head contains a HEPA (high efficiency particulate arresting) filter and directs a steam of air downwardly past the front of the incubator. In operation, the clean air source 30 provides a flow of class 10 clean air (as defined by the United States government in Federal Standard 209 B/C) at a speed of about 0.5 m/s past the front of the incubator.

It will be noted that the filter head extends forward of the front wall of the cabinet by about the same amount as the door when the door is fully opened.

Curtains 46, 48, which may be made of transparent vinyl material, are attached to the two opposite sides of the support frame and hang downwards adjacent the vertical edges of the front wall of the incubator. The curtains constrain the downward flow of clean air so that it does not spread horizontally in directions parallel to the front wall of the cabinet. Therefore, a positive gauge pressure is maintained in the region between the curtains.

The extent of the flowing body of clean air in the direction perpendicular to the front wall of the incubator cabinet is such that airborne particles that enter the flow of air are carried vertically downward below the bottom of the incubator in a shorter time than it would take such Particles to diffuse through the flow of air to the front wall of the cabinet. Accordingly, the flowing body of clean air prevents airborne particles from entering the incubator chamber. Further, when a technician reaches into the incubator chamber, the flow of clean air sweeps particles that might otherwise be deposited in the chamber from the technician's hand and sleeve and prevents deposited therein.

It is common to provide a laboratory incubator with a port in one of the sidewalls of the incubator cabinet in order to allow an accessory, such as a power supply cable, to be introduced into the chamber without its being necessary to leave the door open. In the apparatus shown in FIG. 1, this port 50 is equipped with a hose fitting 52 that is coupled to a hose 54 whose opposite end is presented to the suction side of the fan unit 38.

Thus, a low partial vacuum is established in hose 54 and is communicated to the incubator chamber 28. When the door of the incubator is opened, the partial vacuum in the chamber is relieved by entry of clean air into the chamber 28. This prevents an exchange between the interior of the chamber and the ambient air. The contents of the chamber are protected from contamination, and the user and his environment are protected from possibly hazardous materials in the chamber.

Figure 2:
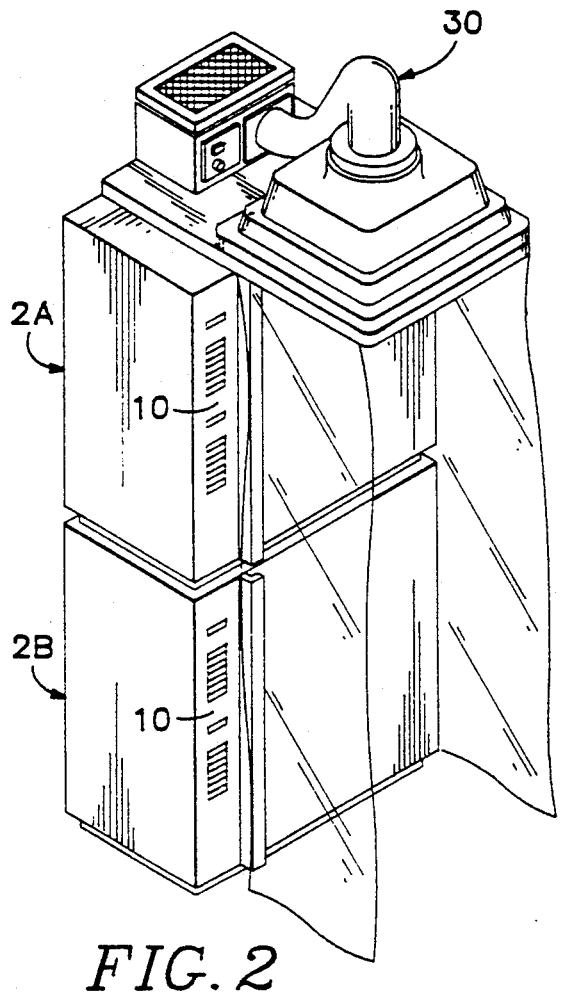
FIG. 2 is a perspective view of a second form of laboratory incubator apparatus embodying the present invention.

FIG. 2 shows a modified form of apparatus in which two self-contained incubators 2A and 2B, each with its own control panel, are mounted one on top of the other, and the clean air source 30 is mounted on top of the upper incubator 2A. The curtains 46, 48 extend downwards from the support frame 28 to the floor on which the lower incubator 2B rests. The density of airborne particles is generally greater within about 30 cm of the floor than elsewhere. The flow of air at the bottom of the lower incubator is constrained so that it must flow away from the lower incubator, and accordingly airborne particles close to the floor are carried away from the incubator.

Figure 3:
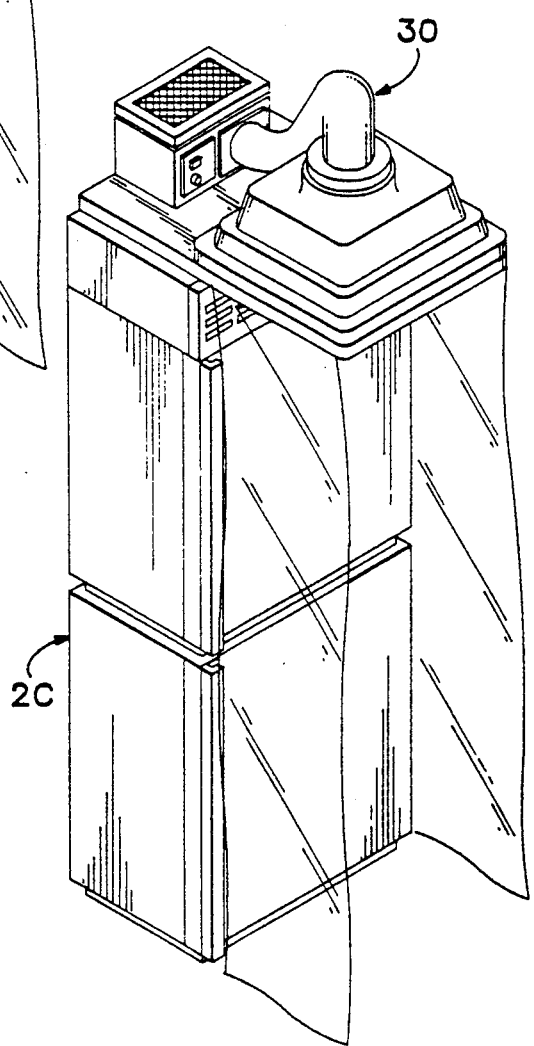
FIG. 3 is a perspective view of a third form of laboratory incubator apparatus embodying the present invention.

FIG. 3 shows an incubator 2C that has two chambers, each provided with its own door, and a single control panel. A clean air source 30 is mounted on top of the incubator 2C.

It will be appreciated that the invention is not restricted to the particular embodiments that have been described, and that variations may be made therein without departing from the scope of the invention as defined in the appended claims and equivalents thereof. For example, it is apparent from FIG. 1 that when the incubator door is open, the door itself serves to guide the flow of clean air provided by the clean air source. Thus, although it is preferred that the clean air source be provided with curtains at each vertical edge of the front wall of the cabinet it is not essential that a curtain be provided at the hinge edge of the door. If the incubator has a double door, comprising two half-doors hinged at the left and right respectively of the door opening, the two half doors guide the air flow at the two opposite vertical edges of the front wall and therefore no curtains are necessary. Moreover, the invention is not restricted to laboratory incubators but is applicable to other kinds of controlled environment apparatus for biological use, such as ovens and refrigerators used for studying the effects of elevated and depressed temperatures on biological materials. Further, the invention is not restricted to the clean air source providing class 10 clean air, and, depending on the application, a source that provides clean air of a higher or lower standard may be used.

We claim:

1. Controlled environment chamber apparatus for maintaining biological material under controlled conditions of temperature and/or humidity, said apparatus comprising a cabinet defining a chamber and having a front wall that defines a chamber opening for providing access to the chamber, at least one door controlling access to the chamber, the door being mounted to the cabinet for pivotal movement between an open position in which access can be had to the interior of the chamber and a closed position in which the chamber opening is blocked, and a clean air source for providing a flow of clean air past the chamber opening, the flow passing outside the chamber when the door is in the closed position.

2. Apparatus according to claim 1, wherein the door is mounted to the chamber is a vertical hinge, and the clean air source comprises a support structure mounted on top of the cabinet and having a portion that projects forward of the cabinet, and at least one curtain suspended from the support structure along an edge of the door opposite the hinge.

3. Apparatus according to claim 2, wherein the clean air source comprises a discharge head mounted on the portion of the support structure that projects forward of the incubator cabinet, and a fan unit connected to the discharge head for supplying air thereto.

4. Apparatus according to claim 3, wherein the fan unit is mounted on the support structure and has an outlet opening connected to the discharge head.

5. Apparatus according to claim 1, wherein the clean air source comprises means for establishing a region of subatmospheric pressure spaced from the front wall of the cabinet, and means for communicating the subatmospheric pressure to the interior of the chamber separately from the chamber opening, whereby clean air is drawn into the chamber when the door is in the open position.

6. Apparatus according to claim 1, wherein the clean air source comprises a fan unit having an inlet opening that is isolated from the chamber when the door is in the closed position.

7. Apparatus according to claim 1, wherein the clean air source comprises a discharge head positioned forward of the cabinet and above the chamber opening, and a fan unit connected to the discharge head for supplying air thereto, whereby the flow of clean air passes the chamber in a downward direction.

8. Apparatus according to claim 1, wherein the clean air source comprises a support structure mounted on top of the cabinet and having a portion that projects forward of the cabinet, a discharge head mounted on the portion of the support structure that projects forward of the incubator cabinet, whereby the flow of clean air passes the chamber in a downward direction, and a curtain suspended from the support structure at one side of the chamber opening.

9. Apparatus according to claim 8, comprising first and second curtains suspended from the support structure at opposite respective sides of the opening for laterally constraining the flow of clean air.

10. Controlled environment chamber apparatus for maintaining biological material under controlled conditions of temperature and/or humidity, said apparatus comprising a cabinet defining a chamber and having a front wall that defines a chamber opening for providing access to the chamber, at least one door for controlling access to the chamber, the door being mounted to the cabinet by a vertical hinge for pivotal movement between an open position in which access can be had to the interior of the chamber and a closed position in which the chamber opening is blocked, and a clean air source for providing a flow of clean air past the chamber opening, the clean air source comprising a support structure mounted on top of the cabinet and having a portion that projects forward of the cabinet, and at least one curtain suspended from the support structure along an edge of the door opposite the hinge.

11. Apparatus according to claim 10, wherein the clean air source comprises s discharge head mounted on the portion of the support structure that projects forward of the incubator cabinet, and a fan unit connected to the discharge head for supplying air thereto.

12. Apparatus according to claim 11, wherein the fan nit is mounted on the support structure and has an outlet opening connected to the discharge head.

13. Apparatus according to claim 10, wherein the clean air source comprises means for establishing a region of subatmospheric pressure spaced from the front wall of the cabinet, and means for communicating the subatmospheric pressure to the interior of the chamber separately from the chamber opening, whereby clean air is drawn into the chamber when the door is in the open position.

14. Controlled environment chamber apparatus for maintaining biological material under controlled conditions of temperature and/or humidity, said apparatus comprising a cabinet defining a chamber and having a front wall that defines a chamber opening for providing access to the chamber, at least one door for controlling access to the chamber, the door being mounted to the cabinet for pivotal movement between an open position in which access can be had to the interior of the chamber and a closed position in which the chamber opening is blocked, and a clean air source for providing a flow of clean air past the chamber opening, the clean air source comprising means for establishing a region of subatmospheric pressure spaced from the front wall of the cabinet, and means for communicating the subatmospheric pressure to the interior of the chamber separately from the chamber opening, whereby clean air is drawn into the chamber when the door is in the open position.

15. Apparatus according to claim 14, wherein the front wall of the cabinet is substantially vertical and the clean air source comprises a support structure mounted on top of the cabinet and having a portion that projects forward of the cabinet.

16. Apparatus according to claim 15, wherein the clean air source comprises a discharge head mounted on the portion of the support structure that projects forward of the incubator cabinet, and a fan unit connected to the discharge head for supplying air thereto.

17. Apparatus according to claim 16, wherein the fan unit is mounted on the support structure and has an outlet opening connected to the discharge head.

* * * * *

UNITED STATES PATENT AND TRADEMARK OFFICE
CERTIFICATE OF CORRECTION

PATENT NO. : 5,169,217

DATED : December 8, 1992

INVENTOR(S) : Kenneth L. Orchard; Frank W. Enderlin

It is certified that error appears in the above-identified patent and that said Letters Patent is hereby corrected as shown below:

Column 1, lines 50-51, before "drawings" insert --accompanying--.

Column 2, line 5, "reference 16a" should read --reference 16b--.

Column 2, line 31, "steam" should read --stream--.

Column 2, line 53, "Particles" should read --particles--.

Column 2, line 60, after "prevents" insert --these particles from entering the chamber and being--.

Column 3, line 60, before "controlling" insert --for--.

Column 4, line 2, "is", second occurrence, should read --by--.

Column 4, line 65, "s" should read --a--.

UNITED STATES PATENT AND TRADEMARK OFFICE
CERTIFICATE OF CORRECTION

PATENT NO. : 5,169,217

DATED : December 8, 1992

INVENTOR(S) : Kenneth L. Orchard; Frank W. Enderlin

It is certified that error appears in the above-identified patent and that said Letters Patent is hereby corrected as shown below:

Column 5, line 2, "nit" should read --unit--.

Signed and Sealed this

Twenty-third Day of November, 1993

Attest:

BRUCE LEHMAN

*Attesting Officer*      *Commissioner of Patents and Trademarks*